United States Patent
Zheng et al.

(10) Patent No.: US 11,957,875 B2
(45) Date of Patent: Apr. 16, 2024

(54) TECHNIQUES AND DEVICES PROVIDING ADAPTIVITY AND PERSONALIZATION IN DIABETES TREATMENT

(71) Applicant: INSULET CORPORATION, Acton, MA (US)

(72) Inventors: Yibin Zheng, Hartland, WI (US); Joon Bok Lee, Acton, MA (US); Steven Cardinali, Tewksbury, MA (US); Jason O'Connor, Acton, MA (US); Eric Benjamin, Cambridge, MA (US); Ian McLaughlin, Groton, MA (US); David Nazzaro, Groveland, MA (US); Ashutosh Zade, San Diego, CA (US)

(73) Assignee: INSULET CORPORATION, Acton, MA (US)

( * ) Notice: Subject to any disclaimer, the term of this patent is extended or adjusted under 35 U.S.C. 154(b) by 777 days.

(21) Appl. No.: 17/112,314

(22) Filed: Dec. 4, 2020

(65) Prior Publication Data
US 2021/0170104 A1 Jun. 10, 2021

Related U.S. Application Data

(60) Provisional application No. 62/944,792, filed on Dec. 6, 2019.

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14248* (2013.01); *G01N 33/49* (2013.01); *G16H 10/60* (2018.01); *G16H 20/17* (2018.01); *G16H 20/60* (2018.01); *G16H 40/40* (2018.01); *G16H 40/67* (2018.01); *G16H 50/30* (2018.01); *G16H 50/70* (2018.01); *A61M 2005/1726* (2013.01);
(Continued)

(58) Field of Classification Search
None
See application file for complete search history.

(56) References Cited

U.S. PATENT DOCUMENTS

| 303,013 A | 8/1884 | Horton |
|---|---|---|
| 2,797,149 A | 6/1957 | Skeggs |

(Continued)

FOREIGN PATENT DOCUMENTS

| AU | 2015200834 A1 | 3/2015 |
|---|---|---|
| AU | 2015301146 A1 | 3/2017 |

(Continued)

OTHER PUBLICATIONS

US 5,954,699 A, 09/1999, Jost et al. (withdrawn)
(Continued)

*Primary Examiner* — Manuel A Mendez
(74) *Attorney, Agent, or Firm* — Goodwin Procter LLP

(57) ABSTRACT

Disclosed are a device, system, methods and computer-readable medium products that provide an updated insulin-to-carbohydrate ratio and an updated total daily insulin. The described processes may be used for periodic updating of the insulin-to-carbohydrate ratio and the total daily insulin. The insulin-to-carbohydrate ratio and/or the total may be used in the calculation of new doses of insulin that a drug delivery device may be commanded to deliver to a user.

20 Claims, 6 Drawing Sheets

(51) Int. Cl.

| | |
|---|---|
| *G01N 33/49* | (2006.01) |
| *G16H 10/60* | (2018.01) |
| *G16H 20/17* | (2018.01) |
| *G16H 20/60* | (2018.01) |
| *G16H 40/40* | (2018.01) |
| *G16H 40/67* | (2018.01) |
| *G16H 50/30* | (2018.01) |
| *G16H 50/70* | (2018.01) |

(52) U.S. Cl.
CPC ... *A61M 2205/505* (2013.01); *A61M 2205/52* (2013.01); *A61M 2230/201* (2013.01)

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |

(56) References Cited

U.S. PATENT DOCUMENTS

| | | |
|---|---|---|
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |

(56) References Cited

U.S. PATENT DOCUMENTS

| | | |
|---|---|---|
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |

(56) References Cited

U.S. PATENT DOCUMENTS

| | | |
|---|---|---|
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 1571582 A2 | 9/2005 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |

(56) References Cited

FOREIGN PATENT DOCUMENTS

| | | | |
|---|---|---|---|
| EP | 2943149 A1 | 11/2015 | |
| EP | 3177344 A1 | 6/2017 | |
| EP | 3314548 A1 | 5/2018 | |
| EP | 1571582 B1 | 4/2019 | |
| EP | 2897071 B1 | 5/2019 | |
| EP | 3607985 A1 | 2/2020 | |
| GB | 2443261 A | 4/2008 | |
| JP | 51125993 A | 11/1976 | |
| JP | 02131777 A | 5/1990 | |
| JP | 2004283378 A | 10/2007 | |
| JP | 2017525451 A | 9/2017 | |
| JP | 2018153569 A | 10/2018 | |
| JP | 2019525276 A | 9/2019 | |
| TW | 200740148 A | 10/2007 | |
| TW | M452390 U | 5/2013 | |
| WO | 9800193 A1 | 1/1998 | |
| WO | 9956803 A1 | 11/1999 | |
| WO | 0030705 A1 | 6/2000 | |
| WO | 0032258 A1 | 6/2000 | |
| WO | 0172354 A2 | 10/2001 | |
| WO | 2002015954 A1 | 2/2002 | |
| WO | 0243866 A2 | 6/2002 | |
| WO | 02082990 A1 | 10/2002 | |
| WO | 03016882 A1 | 2/2003 | |
| WO | 03039362 A1 | 5/2003 | |
| WO | 03045233 A1 | 6/2003 | |
| WO | 2004043250 A1 | 5/2004 | |
| WO | 04092715 A1 | 10/2004 | |
| WO | 2005051170 A2 | 6/2005 | |
| WO | 2005082436 A1 | 9/2005 | |
| WO | 05110601 A1 | 11/2005 | |
| WO | 2005113036 A1 | 12/2005 | |
| WO | 2006053007 A2 | 5/2006 | |
| WO | 2007064835 A2 | 6/2007 | |
| WO | 2007078937 A1 | 7/2007 | |
| WO | 2008024810 A2 | 2/2008 | |
| WO | 2008029403 A1 | 3/2008 | |
| WO | 2008133702 A1 | 11/2008 | |
| WO | 2009045462 A1 | 4/2009 | |
| WO | 2009049252 A1 | 4/2009 | |
| WO | 2009066287 A3 | 5/2009 | |
| WO | 2009066288 A1 | 5/2009 | |
| WO | 2009098648 A2 | 8/2009 | |
| WO | 2009134380 A2 | 11/2009 | |
| WO | 2010053702 A1 | 5/2010 | |
| WO | 2010132077 A1 | 11/2010 | |
| WO | 2010138848 A1 | 12/2010 | |
| WO | 2010147659 A2 | 12/2010 | |
| WO | 2011095483 A1 | 8/2011 | |
| WO | 2012045667 A2 | 4/2012 | |
| WO | 2012108959 A1 | 8/2012 | |
| WO | 2012134588 A1 | 10/2012 | |
| WO | 2012177353 A1 | 12/2012 | |
| WO | 2012178134 A2 | 12/2012 | |
| WO | 2013078200 A1 | 5/2013 | |
| WO | 2013134486 A2 | 9/2013 | |
| WO | 20130149186 A1 | 10/2013 | |
| WO | 2013177565 A1 | 11/2013 | |
| WO | 2013182321 A1 | 12/2013 | |
| WO | 2014109898 A1 | 7/2014 | |
| WO | 2014110538 A1 | 7/2014 | |
| WO | 2014194183 A2 | 12/2014 | |
| WO | 2015056259 A1 | 4/2015 | |
| WO | 2015061493 A1 | 4/2015 | |
| WO | 2015073211 A1 | 5/2015 | |
| WO | 2015081337 A2 | 6/2015 | |
| WO | 2015187366 A1 | 12/2015 | |
| WO | 2016004088 A1 | 1/2016 | |
| WO | 2016022650 A1 | 2/2016 | |
| WO | 2016041873 A1 | 3/2016 | |
| WO | 2016089702 A1 | 6/2016 | |
| WO | 2016141082 A1 | 9/2016 | |
| WO | 2016161254 A1 | 10/2016 | |
| WO | 2017004278 A1 | 1/2017 | |
| WO | 2017091624 A1 | 6/2017 | |
| WO | 2017105600 A1 | 6/2017 | |
| WO | 2017184988 A1 | 10/2017 | |
| WO | 20170184988 A1 | 10/2017 | |
| WO | 2017205816 A1 | 11/2017 | |
| WO | 2018009614 A1 | 1/2018 | |
| WO | 2018067748 A1 | 4/2018 | |
| WO | 2018120104 A1 | 7/2018 | |
| WO | 2018136799 A1 | 7/2018 | |
| WO | 2018204568 A1 | 11/2018 | |
| WO | 2019077482 A1 | 4/2019 | |
| WO | 2019094440 A1 | 5/2019 | |
| WO | 2019213493 A1 | 11/2019 | |
| WO | 2019246381 A1 | 12/2019 | |
| WO | 2020081393 A1 | 4/2020 | |
| WO | 2021011738 A1 | 1/2021 | |

OTHER PUBLICATIONS

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The Nice-Sugar (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Searching Authority, Invitation to Pay Additional Fees, International Application No. PCT/US2006/004929, dated Jul. 27, 2006.

Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A ""Microbial Contamination Of Haemodialysis Catheter Connections"" Journal of Renal Care,European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study".

Wilson, George S., et al., Progress toward the Development of an Implantable Sensor for Glucose, Clin. Chem., vol. 38, No. 9, 1992, pp. 1613-1617.

(56) References Cited

OTHER PUBLICATIONS

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 dated Jul. 16, 2010 (Optis. 247VPC).
International Search Report and Written Opinion in PCT/US2008/079641 (Optis.203VPC) dated Feb. 25, 2009.
Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et. al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.
International Preliminary Report on Patentability for the International Patent Application No. PCT/US2019/053603, dated Apr. 8, 2021, 9 pages.
International Search Report and Written Opinion for the International Patent Application No. PCT/US2019/053603, dated Jan. 7, 2020, 16 pages.
International Search Report and Written Opinion for International Patent Application No. PCT/US2021/051027, dated Jan. 7, 2022, 16 pages.
International Search Report and Written Opinion for International Patent Application No. PCT/US2021/052372, dated Jan. 26, 2022, 15 pages.
International Search Report and Written Opinion for the International Patent Application No. PCT/US2021/046607, dated Jan. 31, 2022, 20 pages.
International Search Report and Written Opinion for the International Patent Application No. PCT/US2021/055745, dated Feb. 14, 2022, 13 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, dated Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, dated May 16, 2017, 12 pages.
International Search Report and Written Opinion for the International Patent Application No. PCT/US2018/018901, dated Aug. 6, 2018, 12 pages.
International Search Report and Written Opinion for International Patent Application No. PCT/US2018/052467, dated Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on IOS 11", GoToTags, Sep. 11, 2017, web <https://gototags.com/blog/read-nfc-tags-with-an-iphone-app-on-ios-11/>. (Year:2017).
International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
International Search Report and Written Opinion for Application No. PCT/US2019/030652, dated Sep. 25, 2019, 19 pages.
International Search Report and Written Opinion for the International Patent Application No. PCT/US2020/052125, dated Aug. 12, 2020, 15 pages.
International Search Report and Written Opinion for the International Patent Application No. PCT/US2020/050332, dated Sep. 12, 2020, 12 pages.
European Patent Office, "Notification of Transmittal of the ISR and the Written Opinion of the International Searching Authority, or the Declaration," in PCT Application No. PCT/GB2015/050248, dated Jun. 23, 2015, 12 pages.
International Search Report and Written Opinion for the International Patent Application No. PCT/US2022/013470, dated May 6, 2022, 14 pages.
International Search Report and Written Opinion for the International Patent Application No. PCT/US2022/013473, dated May 6, 2022, 13 pages.
International Search Report and Written Opinion for the International Patent Application No. PCT/US2022/019079, dated Jun. 2, 2022, 14 pages.
International Search Report and Written Opinion for the International Patent Application No. PCT/US2022/018453, dated Jun. 2, 2022, 13 pages.
International Search Report and Written Opinion for the International Patent Application No. PCT/US22/018700, dated Jun. 7, 2022, 13 pages.

(56) References Cited

OTHER PUBLICATIONS

International Search Report and Written Opinion for the International Patent Application No. PCT/US22/019080, dated Jun. 7, 2022, 14 pages.
International Search Report and Written Opinion for the International Patent Application No. PCT/US22/019664, dated Jun. 7, 2022, 14 pages.
International Search Report and Written Opinion for the International Patent Application No. PCT/US21/060618, dated Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, dated Apr. 22, 2022, 15 pages.
European Search Report for the European Patent Application No. 21168591.2, dated Oct. 13, 2021, 04 pages.
International Search Report and Written Opinion for the International Patent Application No. PCT/US2021/041954, dated Oct. 25, 2021, 13 pages.
International Search Report and Written Opinion for the International Patent Application No. PCT/US2021/047771, dated Dec. 22, 2021, 11 pages.
International Search Report and Written Opinion for the International Patent Application No. PCT/US2021/052855, dated Dec. 22, 2021, 11 pages.
International Search Report and Written Opinion for the International Patent Application No. PCT/US2021/022694, dated Jun. 25, 2021, 13 pages.
International Search Report and Written Opinion for the International Patent Application No. PCT/US2020/063326, dated May 3, 2021, 17 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,vol. Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
International Search Report and Written Opinion for the International Patent Application No. PCT/US2021/012246, dated Apr. 13, 2021, 15 pages.
International Search Report and Written Opinion for the International Patent Application No. PCT/US2021/013639, dated Apr. 28, 2021, 14 pages.
An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.
International Search Report and Written Opinion for the International Patent Application No. PCT/US2021/017441, dated May 25, 2021, 12 pages.
International Search Report and Written Opinion for the International Patent Application No. PCT/US2021/017664, dated May 26, 2021, 16 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, dated May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, dated May 27, 2021, 16 pages.
International Search Report and Written Opinion for the International Patent Application No. PCT/US2020/065226, dated May 31, 2021, 18 pages.
International Search Report and Written Opinion for the International Patent Application No. PCT/US2021/017659, dated May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

(56) References Cited

OTHER PUBLICATIONS

E. Atlas et al., "MD-Logic Artificial Pancreas System: A pilot study in adults with type 1 diabetes", Diabetes Care, vol. 33, No. 5, Feb. 11, 2010, pp. 1071-1076.
Anonymous: "Fuzzy control system", Wikipedia, Jan. 10, 2020. URL: https://en.wikipedia.org/w/index.php?title=Fuzzy_control_system&oldid=935091190 Retrieved: May 25, 2021.
International Search Report and Written Opinion for the International Patent Application No. PCT/US2021/016283, dated Jun. 2, 2021, 15 pages.

161

162 — Receive an approximate amount of carbohydrates ingested in a meal

163 — Determine an amount of insulin onboard in a post prandial time period

165 — Determine an error factor representing an amount of insulin over or under delivered during the post prandial period 167 — Determine a difference between the determined amount of insulin onboard and the error factor 168 — Calculate an updated insulin to carbohydrate ratio based on the determined difference and the approximate amount of carbohydrates ingested 169 — Modify delivery of insulin based on the updated insulin to carbohydrate ratio

FIG. 1C

TECHNIQUES AND DEVICES PROVIDING ADAPTIVITY AND PERSONALIZATION IN DIABETES TREATMENT

CROSS-REFERENCE TO RELATED APPLICATIONS

This application claims the benefit of the filing date of U.S. Provisional Application Ser. No. 62/944,792, filed Dec. 6, 2019, the entire contents of which are incorporated herein by reference in their entirety.

BACKGROUND

An insulin-carbohydrate (IC) ratio, which is conversion factor of number of carbohydrates to units of insulin to be delivered, enables a user or a diabetes management device to calculate an amount of insulin to be delivered when about to eat a meal or after eating a meal. This IC ratio may be periodically tuned. However, presently, an adjustment to a user's insulin-carbohydrate (IC) ratio is a physician modification of the IC ratio after a manual review of each person's blood glucose measurement and insulin delivery histories, which may occur after as long as 3-6 months between physician visits. It would be beneficial if an artificial pancreas algorithm were operable to adjust the IC ratio on a more regular basis.

In addition, user's do not regularly tune their insulin-to-carbohydrate (IC) ratio, and when they do the user's often mistune the IC ratios, leading to users experiencing post prandial hyperglycemia due to under-bolusing (i.e., delivering too little insulin with a mealtime bolus dosage) or post prandial hypoglycemia due to over-bolusing (i.e., delivering too much insulin with a mealtime bolus dosage).

In other situations, a user's Total Daily Insulin (TDI) values may be determined by taking a simple sum of the user's insulin delivery throughout one day. This value is usually calculated by taking the sum of all insulin delivery to the user each day. However, this manner of determining TDI does not consider the quality of glucose control for the user—if the user consistently experiences hyperglycemia and underdelivers insulin, this manner of determining a quantity of TDI may continue to underestimate the TDI in which case the TDI remains low and may not accurately represent the user's true daily insulin needs. Accordingly, a new manner of determining a user's TDI that maintains the user's blood glucose measurement values within a "normal" range of approximately 70 mg/dL and 180 mg/dL.

It would also be helpful to provide processes, computer products, devices and techniques to assist users with the management of their diabetes treatment plan and overcome the deficiencies described above.

BRIEF DESCRIPTION OF THE DRAWINGS

FIG. 1C shows a flow chart of an example of an alternate process for determining an insulin-carbohydrate ratio.

DETAILED DESCRIPTION

Figure 1A:
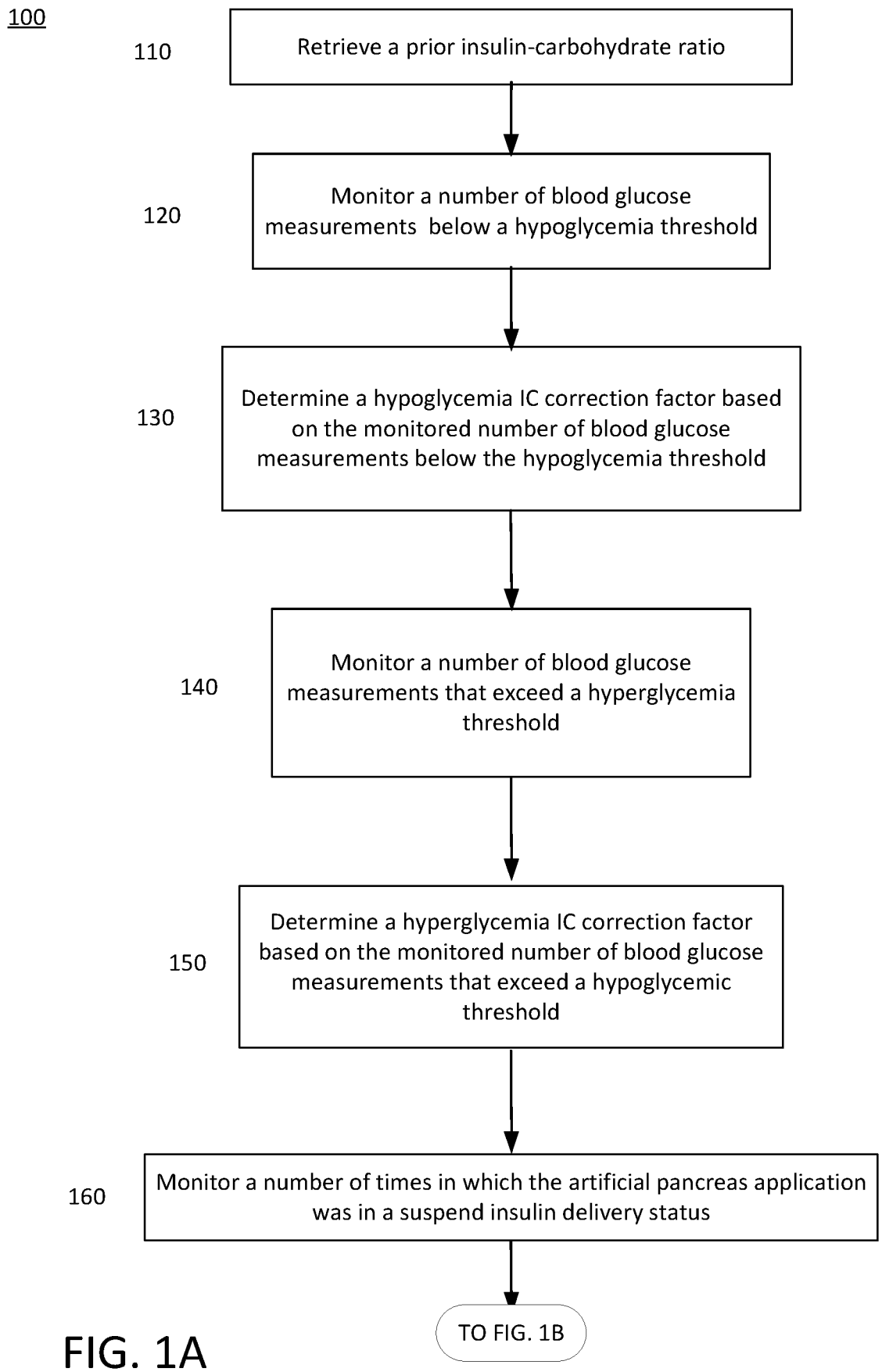
FIGS. 1A and 1B show a flow chart of an example of a process for determining an insulin-carbohydrate ratio.

Various examples provide a method, a system, a device and a computer-readable medium for addressing issues related to updating a user's insulin to carbohydrate ratio that is used to determine meal time bolus dosages and functions for updating a user's total daily insulin that are used to update user's basal insulin doses.

A user's Total Daily Insulin (TDI) value is a simple sum of the user's all insulin needs throughout one day. This value is usually calculated by taking the sum of all insulin delivery to the user each day. However, this does not account for the quality of glucose control for the user—if the user consistently experiences hyperglycemia and underdelivers insulin, this TDI quantity will remain low and will not represent the user's true daily insulin needs.

Another example provides a process that may be used with any additional algorithms or computer applications that manage blood glucose levels and insulin therapy. Such algorithms may be referred to as an "artificial pancreas" algorithm-based system, or more generally, an artificial pancreas (AP) application, that provides automatic delivery of an insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dL to 120 mg/dL, which is a range satisfying the clinical standard of care for treatment of diabetes. However, an AP application as described herein may be able to establish a target blood glucose value more precisely and may set the target blood glucose value at, for example, 110 mg/dL, or the like. As described in more detail with reference to the examples of FIGS. 1A-4, the AP application may utilize the monitored blood glucose values and other information to generate and send a command to a medical device including, for example, a pump, to control delivery of insulin to the user, change the amount or timing of future doses, as well as to control other functions based on the tuned IC ratio or new TDI calculation.

In contrast to consistently mistuning a user's insulin-carbohydrate ratio (IC), it would be more advantageous to deliver an optimal amount of insulin based on an optimal IC ratio. In some examples, the optimal IC ratio may be the ratio that is used to calculate the amount of insulin to accompanying a meal bolus that would minimize the excursions in blood glucose measurements due to the meal injection. The IC ratio is number of carbohydrates to units of insulin to be delivered. An optimal IC ratio provides the user with an exact or nearly-exact amount of insulin to compensate for the user's intake of carbohydrates. There may be a tolerance with this, for example, so that the blood glucose falls within the blood glucose level range of 70-180 mg/dL, but the intent is to provide an amount of insulin in the mealtime bolus that results in the blood glucose measurement to be at a target blood glucose level of approximately 120 mg/dL, or the like. While 70 mg/dL-120 mg/dL is an optimal range for a user's blood glucose measurement value, a normal blood glucose measurement range—where normal is a blood glucose measurement value that is considered neither hypoglycemic or hyperglycemic—may be between 70 mg/dL and 180 mg/dL.

Figure 1B:
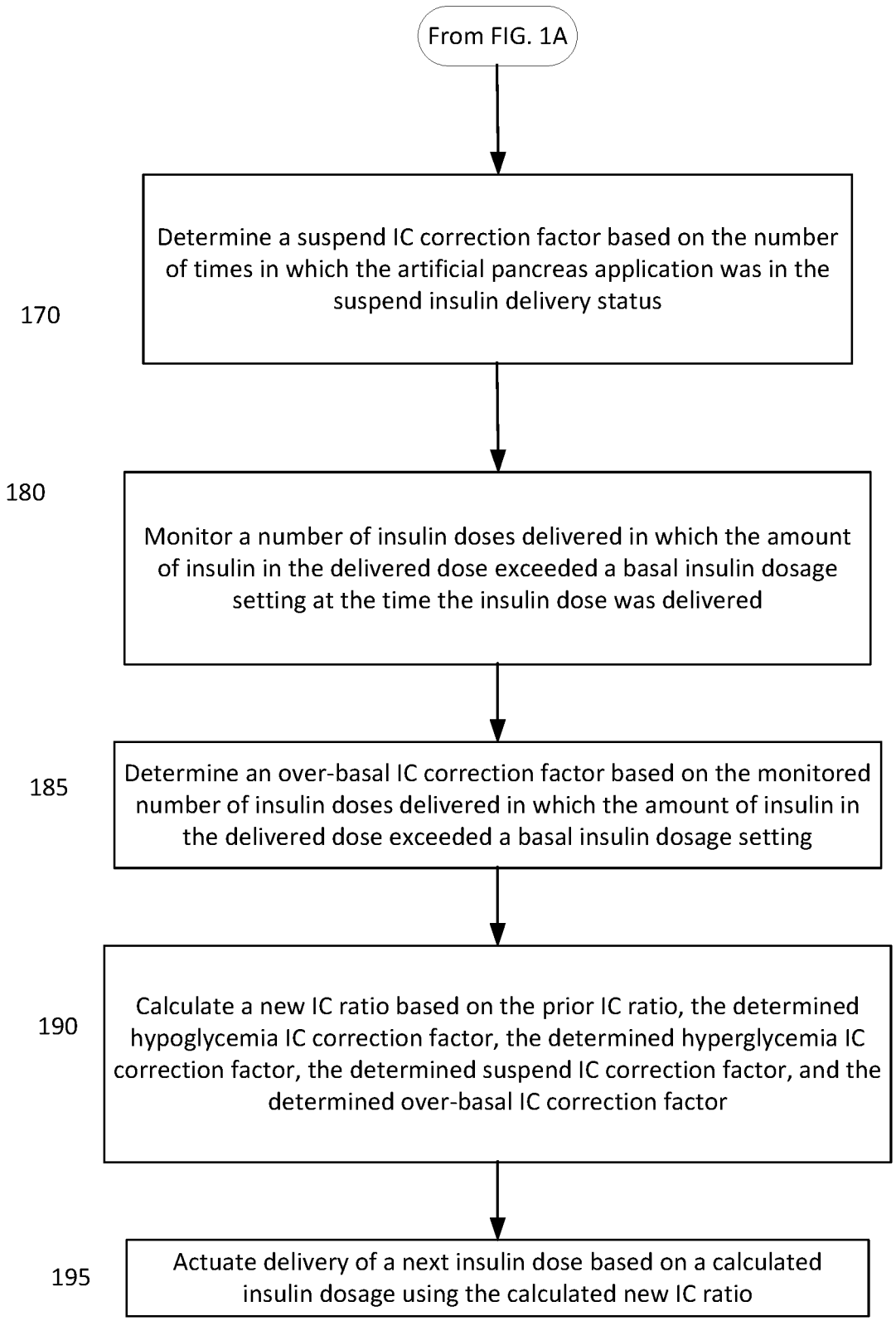

FIGS. 1A and 1B show a flowchart of a process example for determining an insulin-carbohydrate ratio. The process 100 may be implemented by programming code that is executed by a processor a d may utilize a user's glucose concentration and insulin delivery values to identify and correct IC ratios to a more optimal value.

For example, modification of IC ratios may be based on actual hyperglycemic or hypoglycemic blood glucose levels measured following mealtime boluses. In an example, correlation of glucose excursions to insulin-on-board (JOB) traces following mealtime boluses may be determined using the number of blood glucose measurements made before, during, and after meal times. Of course, the use of artificial pancreas algorithm enables a more accurate determination of a correlation, which results in a better estimate of JOB.

In a first example as shown in FIGS. 1A and 1B, a user's post prandial glucose control quality can be assessed in terms of a % times, number of times, or amount of time, the user's measured blood glucose levels are in the hyperglycemic (>180 mg/dL), hypoglycemic (<70 mg/dL), and safe glycemic (70-180 mg/dL) ranges. For example, if the user experiences a high incidence of hypoglycemia (i.e., a large % times, number of times, or amount of time with a blood glucose measurement less than (<) 70 mg/dL), it may indicate that the user may have over-bolused for a meal, leading to a possible recommendation for an increase in the insulin to carbohydrate ratio. Alternatively, if the user experiences a high incidence of hyperglycemia, this may indicate that the user may have under-bolused for a meal, leading to a possible recommendation for a decrease in the insulin to carbohydrate ratio.

In closed loop examples (such as when the artificial pancreas application is managing the user's diabetes treatment plan), if the accompanying closed loop algorithm suspends significantly following boluses, even if the user's glucose control is favorable, this may lead to a recommendation to increase the IC ratio.

In closed loop examples, if the accompanying closed loop algorithm delivers significant amount of insulin above basal following boluses, even if the user's glucose control is favorable, this may lead to a recommendation of decrease in IC ratios.

In the example equation No. 1 below, the adjustment (i.e., $IC_{new}$) can be implemented as:

$$IC_{new1} = IC_{old}\left(1 + \sum_{i=1}^{N} \frac{t_{hypo}(N)}{72}\right)\left(1 - \sum_{i=1}^{N} \frac{t_{hyper}(N)}{72}\right) \quad \text{Eq. 1}$$
$$\left(1 + \sum_{i=1}^{N} \frac{t_{suspend}(N)}{72}\right)\left(1 - \sum_{i=1}^{N} \frac{t_{delivery\ above\ basal}(N)}{72}\right)$$

In Equation No. 1 above, N is the number of meals per day, and various t variables indicate the corresponding 6 hour post-prandial periods that meet each of the four conditions that lead to IC ratio adjustment. The denominator value 72 in each factor is a post prandial period factor and is based on 6 hours times 12 blood glucose measurements (by a continuous blood glucose monitor) per hour which equals 72. For example, a continuous blood monitor (CGM) takes a blood glucose measurement approximately every 5 minutes. The blood glucose measurement may be delivered to a processor monitoring the blood glucose of the user. The denominator value in the respective factors of equation No. 1 may be changed to more closely mirror a user's requirements or physiology.

In the example of FIG. 1, this adjustment may be conducted once per day or less frequently. In another example, the intensity of these adjustments may be modified based on the value of the blood glucose measurement values.

For example, a processor may execute programming code, such as an artificial pancreas application, stored in a memory accessible by the processor. The processor when executing the programming code is operable to perform various functions. For example, the various functions may include obtaining a prior insulin-carbohydrate ratio (e.g., $IC_{old}$) (110) from a memory, via an input to an input device coupled to the processor, or, via a communication from an external source, such as a cloud-based diabetes treatment plan management system or the like. For example, the prior insulin-carbohydrate ratio may be stored in a memory, such as, for example, in a settings file or the like coupled to the processor that is used by the artificial pancreas application in the calculation of dosage settings by the artificial pancreas application.

For a period of time (e.g., 6 hours, 12 hours or the like), different parameters related to blood glucose measurements and management of a diabetes treatment plan may be monitored by a processor. Note that the period of time may begin after the user has a meal, just before the user has a meal, after the user completes a meal, or the like. For example, the processor may receive blood glucose measurement values from a continuous glucose monitor or the like. In the example, the processor may, at 120, monitor the received blood glucose measurement values to determine the number of received blood glucose measurement values that are below a hypoglycemic threshold value (e.g., less than 70 mg/dL). For example, the processor may, as part of the monitoring, compare each received blood glucose measurement value to a hypoglycemic threshold value and increment a hypoglycemia counter if the received blood glucose measurement value is below the hypoglycemic threshold value.

At 130, the processor may determine a hypoglycemia IC correction factor based on the monitored number of blood glucose measurements below the hypoglycemic threshold. The hypoglycemia IC correction factor is represented by factor shown the first parenthetical in Eq. 1:

$$\left(1 + \sum_{i=1}^{N} \frac{t_{hypo}(N)}{72}\right).$$

The hypoglycemia IC correction factor may be used to increase the new IC ratio if an amount of time that blood glucose measurements are below the hypoglycemic blood glucose measurement value, e.g., less than 70 mg/dL, which is a clinical threshold value for hypoglycemia. In the example, the monitored number may be converted into a time parameter. For example, the monitored number of blood glucose that are below the hypoglycemic blood glucose measurement value may be multiplied by 5 minutes, which is the amount of time between blood glucose measurements.

The processor, at 140, may monitor the number of blood glucose measurement values that exceed a hyperglycemia threshold. For example, the processor may monitor the received blood glucose measurement values to determine the number of received blood glucose measurement values that exceed a hyperglycemic threshold value (e.g., greater than 180 mg/dL). For example, the processor, as part of the monitoring, may compare each received blood glucose measurement value to a hyperglycemic threshold value and increment a hyperglycemia counter if the received blood glucose measurement value is greater than the hyperglycemic threshold value.

The processor may determine a hyperglycemia IC correction factor based on the monitored number of blood glucose measurements that exceed a hypoglycemic threshold (150). In the example, the hyperglycemia IC correction factor is represented by the factor shown in the second parenthetical in Eq. 1:

$$\left(1 - \sum_{i=1}^{N} \frac{t_{hyper}(N)}{72}\right).$$

The hyperglycemia IC correction factor may be used to reduce the new IC ratio if the amount of time that the blood glucose measurements are above the hyperglycemia blood glucose measurement value, e.g., greater than 180 mg/dL, which is a clinical threshold for hyperglycemia.

At 160, the processor may monitor the number of times (or amount of time) the artificial pancreas application was in a suspend insulin delivery status. For example, the artificial pancreas application may determine that the delivery of insulin has exceeded their needs so a processor executing the artificial pancreas application may suspend the delivery of insulin including basal insulin doses. The artificial pancreas application may monitor the number of times or the total time that the delivery of insulin is suspended either by a user input or by a suspend delivery process determination made by the artificial pancreas application. The artificial pancreas application may be operable to determine an amount of insulin a person has in their body, referred to as insulin onboard (JOB). The IOB may be determined a number of ways and may be based on amounts of insulin delivered, a user's insulin sensitivity, duration of insulin action and the like. If the IOB is too great, the artificial pancreas application may suspend further delivery of insulin to prevent a user's blood glucose measurement values from falling outside the range of 70 mg/dL-180 mg/dL.

The suspend IC correction factor in the third parenthetical is based on an amount of time that the delivery of insulin was suspended so that may indicate the over-delivery of insulin and a subsequent stoppage in delivery in an attempt to compensate for the over-delivery of insulin. For example, the processor, as part of the monitoring, may receive a suspend delivery signal from a suspend delivery process of the artificial pancreas application. The processor may note a time at which the suspend delivery signal was received, and later note a time at which a resume delivery signal is received. The suspend delivery signal causes the delivery of insulin to be suspended, while the resume delivery signal cause to the delivery of insulin to be resumed. Alternatively, the delivery of insulin may be suspended for a predetermined period of time in response to the suspend delivery signal. For example, the predetermined period to time may be 30 minutes, 1 hour, 4 hours, or longer. In this alternative, the processor may keep track of the number of times N insulin delivery is suspended, for example, based on the number of times that the suspend delivery signal was initiated or received over a given period of time (e.g., 72 hours or the like). Using the predetermined period of time for suspending insulin delivery and the number of times N, an amount of time in which the delivery of insulin was suspended may be determined and may be used to determine a third factor in the IC ratio adjustment as shown in the third parenthetical of Equation No. 1 above. Pharmacokinetics (PK) and pharmacodynamics (PD) of the drug with respect to the user may be relevant to the third and fourth parenthetical factors.

At 170, for example, the processor may determine a suspend IC correction factor based on the number of times in which the artificial pancreas application was in the suspend insulin delivery status. The determined value of the suspend IC correction factor in the third parenthetical may be used to increase the IC ratio so that future instances of over-delivery are reduced. In the third factor:

$$\left(1 + \sum_{i=1}^{N} \frac{t_{suspend}(N)}{72}\right).$$

The variable $t_{suspend}$ (i.e., Tsuspend) stands for an amount of time that the artificial pancreas application was suspended from delivering insulin, and N may refer to the number of times the suspend delivery signal was received.

The processor may further monitor a number of insulin doses delivered in which the amount of insulin in the delivered dose exceeded a basal insulin dosage setting at the time the insulin dose was delivered (180). For example, a basal insulin dose may be 0.5 U/hour, while the actual delivered dosage was 1.5 U/hour. The artificial pancreas application executing on the processor may be operable to determine an over-basal IC correction factor based on the monitored number of insulin doses delivered in which the amount of insulin in the delivered dose exceeded a basal insulin dosage setting (185). In 185, the over-basal IC factor in the fourth parenthetical is an indication of under-delivery if the algorithm is frequently delivering over the user's basal profile. If the artificial pancreas application is delivering insulin above the basal threshold, the artificial pancreas application is attempting to compensate for the user's increased glucose needs. Therefore, the IC ratio may be decreased based on the time that the automatic insulin delivery as controlled by the artificial pancreas application is delivering more insulin than the user's basal needs.

Upon the determination of the hypoglycemia IC correction factor, the hyperglycemia IC correction factor, the suspend IC correction factor and the over-basal IC correction factor, the artificial pancreas application executing on the processor may, at 190, calculate a new IC ratio (i.e., $IC_{new1}$). The new IC ratio, $IC_{new1}$, may be based on the prior IC ratio, the determined hypoglycemia IC correction factor, the determined hyperglycemia IC correction factor, the determined suspend IC correction factor, and the determined over-basal IC correction factor, as shown in Equation No. 1.

The artificial pancreas application may determine a new insulin dosage for the next delivery of insulin using the new IC ratio (i.e., $IC_{new1}$). The artificial pancreas application may actuate delivery of a next insulin dose based on a calculated insulin dosage using the calculated new IC ratio (195).

In the forgoing examples, the respective factors included a post prandial period factor of 72. The post prandial period factor of 72 is based on 6 hours of a post prandial period. The post prandial factor may be calculated as 6 hours times 12 blood glucose measurements per hour (every 5 minutes)

equals 72). The post prandial period factor may be adjusted or tuned for the proper prandial period as needed. The 6 hours may be considered a basis for delivered insulin action. Of course, a post prandial period other than 6 hours may be used. For example, 12 hours, 3 hours or the like may be used depending on the meal (e.g., breakfast may be one time period, while lunch or dinner may be a different period of time).

In another example, the two factors, hypoglycemia IC correction factor and the hyperglycemia IC correction factor, may be used with or without an automatic insulin delivery (AID) algorithm such as that provided by an artificial pancreas application. However, if an AID algorithm of an artificial pancreas application is being used, the suspend IC correction factor and the over-basal IC correction factor may also be used.

Another option for adjusting the IC ratio is also provided. In this other option, the IC ratio modification may be based on known blood glucose measurement values and insulin onboard (IOB) traces. The IOB may be used to estimate how much insulin is in a user's body. For example, an insulin dosage recommendation may be 10 units of insulin. However, the user may have 3 units of IOB. As a result, the dosage recommendation may be reduced by simple subtraction from 10 units of insulin to 7 units of insulin (10 units of recommended dosage minus 3 units of IOB (which the body still needs to process)).

In another example, the user's post prandial blood glucose measurements and insulin traces can be correlated to determine if the IOB values sufficiently compensate for the resulting glucose excursions following the meals.

Any residual IOB that is consumed beyond the glucose excursions can be correlated with IOB values that properly compensated for meal ingestion.

This correlation can then be utilized to identify the correct IC ratios based on known user input values.

In the example, this adjustment can be implemented as shown in Equation No. 2 below:

$$IC_{new2} = \frac{\sum_{i=1}^{t} IOB_{post\ prandial}(i) - \sum_{i=1}^{t} \frac{CGM(i) - target(i)}{CF(i)}}{CHO_{meal}} \quad \text{Eq. No. 2}$$

In the example of Equation No. 2, this IC estimate can be calculated for each meal that is ingested and provide an IC ratio profile that is customized to each user's meal. In the example, the numerator is a calculation of the amount of insulin that a user needs in the post prandial period (e.g., 6 hours after a meal) to compensate for the meal. The first term in the numerator, the IOB post prandial term, is the amount of insulin that a user has received during the post prandial period. While the second term, insulin delivery correction term, is an amount of insulin that would have enabled the user to meet their target blood glucose setting. The insulin delivery correction term may either be positive (meaning the user could have used more insulin) or negative (meaning the user could have used less insulin). The denominator is the amount of carbohydrates that were in a meal which is represented by the variable $CHO_{meal}$. This equation (i.e., Equation No. 2) provides the IC ratio (insulin over carbohydrates) that provides the ICnew2.

This process may be done for each meal until there is a convergence to an optimal IC ratio.

A process example illustrating the implementation of the Equation No. 2 is shown in FIG. 1C. In the example of FIG. 1C, the artificial pancreas application executing on a processor 161 may receive, at 161, an approximate amount of carbohydrates ingested in a meal or to be ingested in a meal (162). The artificial pancreas application may keep track or monitor the delivery of insulin over a period of time once it is determined that a meal is ingested, or to be ingested (163). For example, after users indicate a meal ingestion through the request of a meal bolus command, the process implemented by the AP application may consider a number of hours (e.g. 6 hours) as the post prandial period. The artificial pancreas application may keep track of the dosages of insulin delivered during the post prandial time period by a drug delivery device (operable to automatically deliver insulin) or based on inputs from a user regarding dosages of insulin delivered to a user. The artificial pancreas application may be operable to determine an error factor representing an amount of insulin over or under delivered during the post prandial period (165). For example, the artificial pancreas application may receive blood glucose measurements (labeled as CGM in Eq No. 2) during the post prandial period. In the determination of the error factor, the artificial pancreas application may determine a difference between a received blood glucose measurement to the target blood glucose setting for that particular iteration. The differences may be summed during the post prandial period. The summed differences may then be divided by a correction factor that accounts for the user's ability to process delivered insulin.

At 167, the artificial pancreas application may be operable to determine a difference between the determined amount of insulin onboard and the error factor. This determination provides an amount of insulin that the user was estimated to require to compensate for the ingestion of the meal.

The artificial pancreas application may be operable to calculate an updated insulin to carbohydrate ratio based on the determined difference and the approximate amount of carbohydrates ingested (168). The calculated updated insulin (i.e., $IC_{new2}$ in Equation No. 2) may be stored by the artificial pancreas application in a memory of a mobile device. The artificial pancreas application may use the calculated updated insulin in further calculations of dosages of insulin to be delivered by a drug delivery device or by a user.

For example, the artificial pancreas application may be operable make a new calculation of a dosage, such as a basal dosage, a bolus dosage (for a next meal), or the like, based on the calculated updated insulin (i.e., ICnew2 in Equation No. 2). At 169, the artificial pancreas application may be operable to modify delivery of insulin based on the updated insulin to carbohydrate ratio (i.e., $IC_{new2}$). The modified delivery of insulin may be a newly calculated amount of insulin to be delivered in a next dosage, a time of the next dosage, or both a modification of the amount of insulin to be delivered and a time of the delivery of a next dose of insulin.

In another example, the accuracy of the ICnew1 or ICnew2 as determined according to the examples of FIGS. 1A and 1B that utilize Equation Nos. 1 and 2 may be confirmed using the following rules. For example, the new IC ratio can be compared with a correction factor (CF) that is calculated based on the user's average glucose excursions divided by the user's average insulin delivery excursions beyond the basal value. This ratio can be converted into an estimated TDI based on:

$$\frac{1800}{TDI} = CF_{estimate}$$

$$TDI_{estimate} = 1800 CF_{estimate}$$

This TDI can then be converted to an estimated IC from this TDI estimate based on the 800 heuristic as follows:

$$IC_{estimate} = \frac{800}{TDI_{estimate}}$$

Based on a comparison of the new IC ratio (e.g., ICnew1 or ICnew2) to the estimated IC (i.e., $IC_{estimate}$), the artificial pancreas application may be operable to confirm that the new IC ratio was accurately calculated and are within a specified tolerance, such as a range. Based on the determination that the calculation of the new IC ratio by the artificial pancreas application is within a predetermined tolerance of the estimated IC, the artificial pancreas application may continue modification of the delivery of insulin. Conversely, if the determination that the calculation of the new IC ratio by the artificial pancreas application is not within a predetermined tolerance of the estimated IC, the artificial pancreas application may perform a further update of the IC ratio using additional blood glucose measurements received since the previous calculation of the new IC ratio, or the like.

Figure 2:
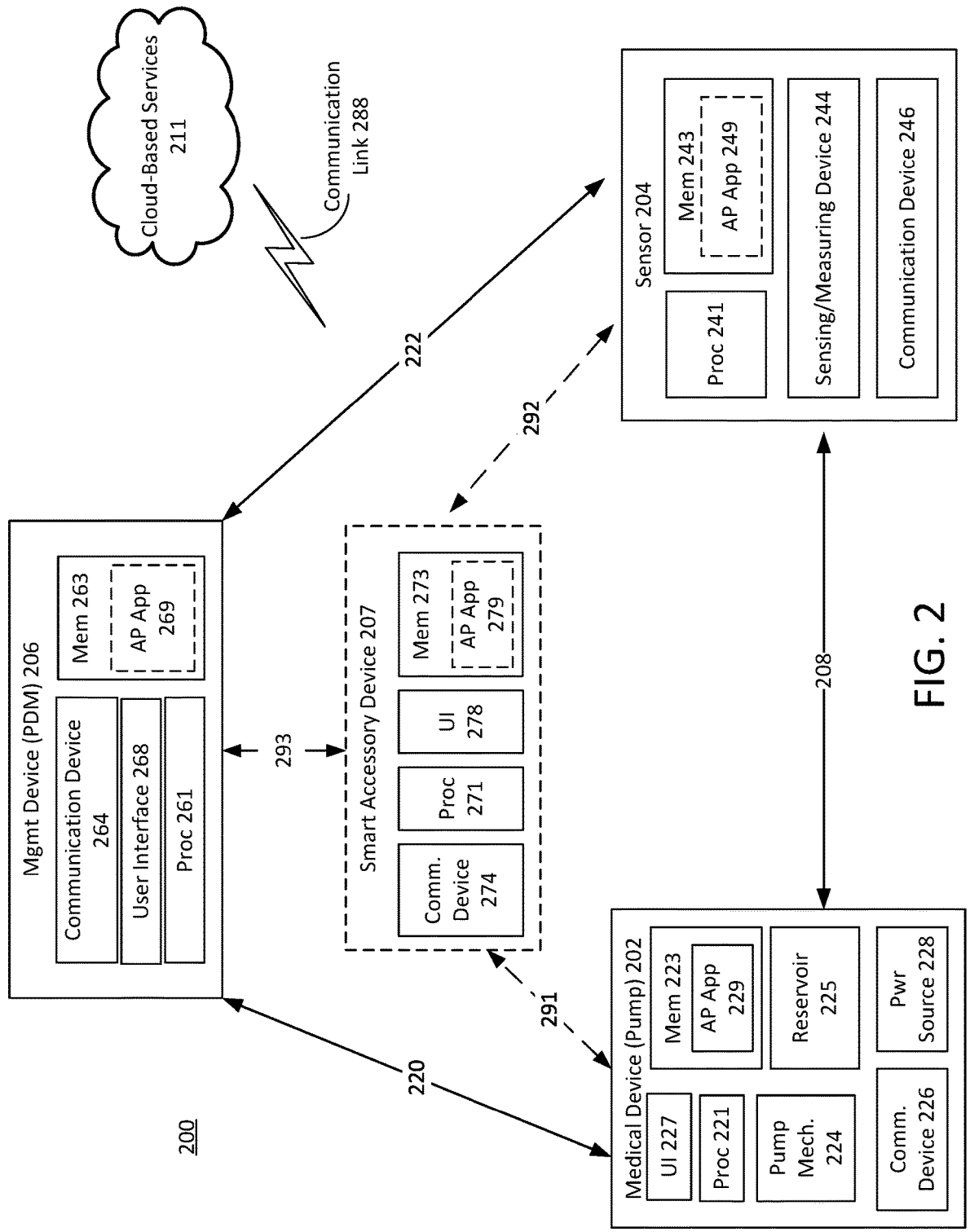
FIG. 2 illustrates a functional block diagram of drug delivery system suitable for implementing the example processes and techniques described herein.
Figure 3:
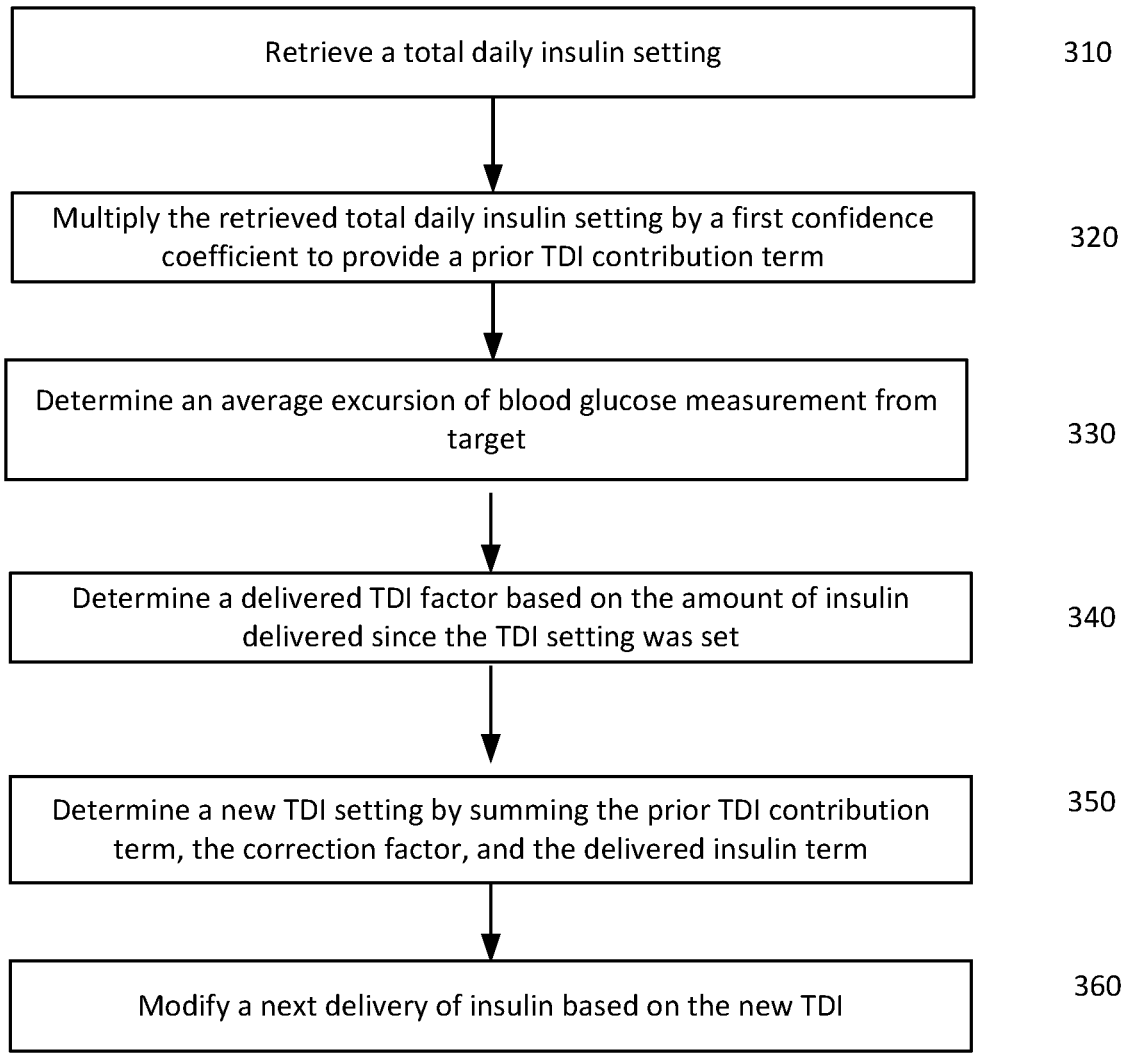
FIG. 3 illustrates a flow chart of an example process for determining a bolus dosage that is to be administered in response to consumption of a meal.
Figure 4:
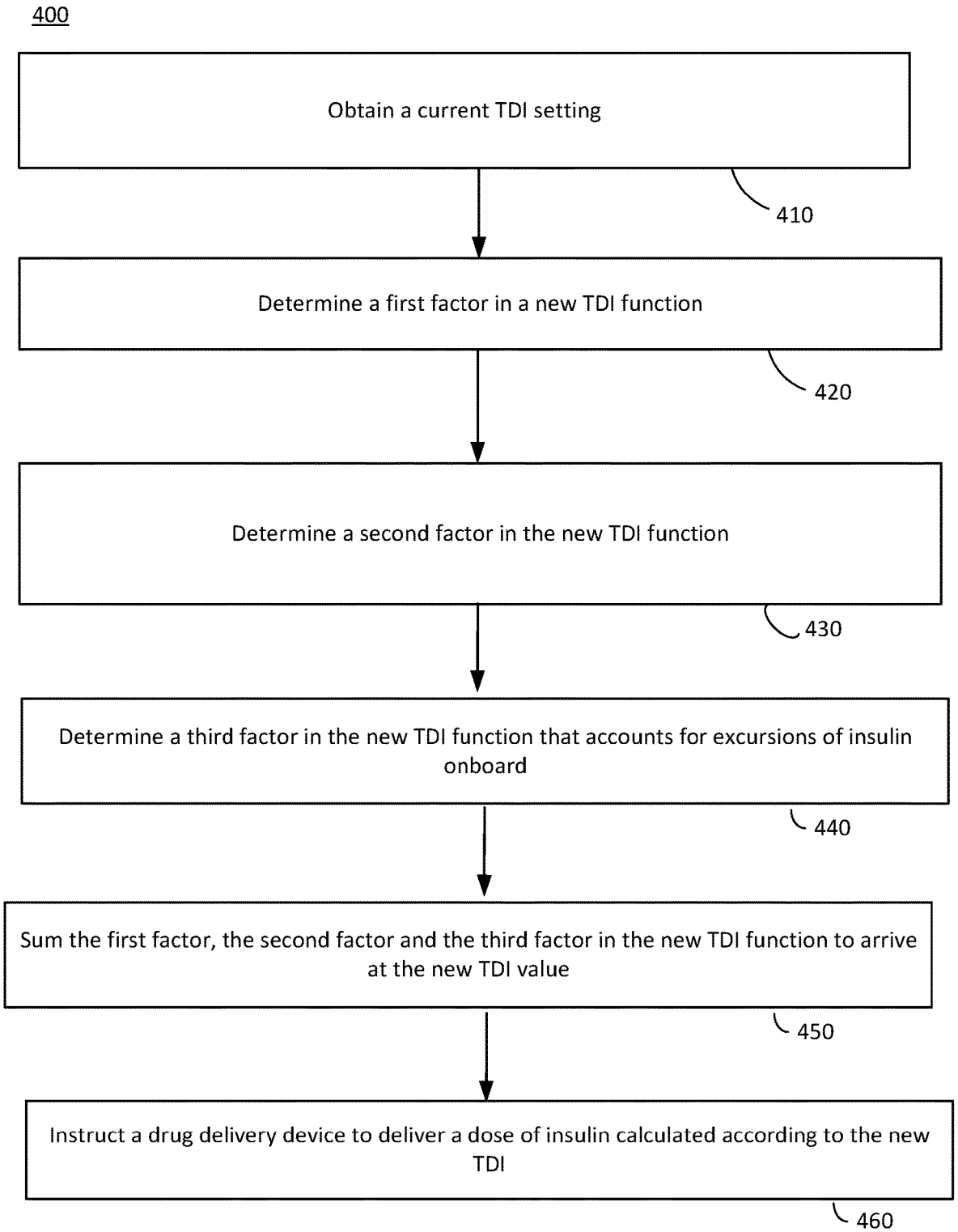
FIG. 4 illustrates a flow chart of another example of a process for determining a dosage of a bolus injection for correcting a blood glucose value.

It may be helpful to discuss an example of a drug delivery system that may implement the process examples of FIGS. 1A-C as well as the examples of FIGS. 3 and 4. FIG. 2 illustrates an example of a drug delivery system 200.

The drug delivery system 200 may be operable to implement an AP application that includes functionality to determine a bolus dosage, output an indication of the determined bolus dosage to actuate delivery of the bolus of insulin based on the indication of the determined bolus dosage. The drug delivery system 200 may be an automated drug delivery system that may include a medical device (pump) 202, a sensor 204, and a management device (PDM) 206. The system 200, in an example, may also include a smart accessory device 207, which may communicate with the other components of system 200 either via a wired or wireless communication link.

In an example, the medical device 202 may be attached to the body of a user, such as a patient or diabetic, and may deliver any therapeutic agent, including any drug or medicine, such as insulin or the like, to a user. The medical device 202 may, for example, be a wearable device worn by the user. For example, the medical device 202 may be directly coupled to a user (e.g., directly attached to a body part and/or skin of the user via an adhesive or the like). In an example, a surface of the medical device 202 may include an adhesive to facilitate attachment to a user.

The medical device 202 may, for example, include a number of components to facilitate automated delivery of a drug (also referred to as a therapeutic agent) to the user. The medical device 202 may be operable to store the drug and to provide the drug to the user. The medical device 202 is often referred to as a pump, or an insulin pump, in reference to the operation of expelling a drug from the reservoir 225 for delivery to the user. While the examples refer to the reservoir 225 storing insulin, the reservoir 225 may be operable to store other drugs or therapeutic agents, such as morphine or the like, suitable for automated delivery.

In various examples, the medical device 202 may be an automated, wearable insulin delivery device. For example, the medical device 202 may include a reservoir 225 for storing the drug (such as insulin), a needle or cannula (not shown) for delivering the drug into the body of the user (which may be done subcutaneously, intraperitoneally, or intravenously), and a pump mechanism (mech.) 224, or other drive mechanism, for transferring the drug from the reservoir 225, through a needle or cannula (not shown), and into the user. The pump mechanism 224 may be fluidly coupled to reservoir 225, and communicatively coupled to the processor 221. The medical device 202 may also include a power source 228, such as a battery, a piezoelectric device, or the like, for supplying electrical power to the pump mechanism 224 and/or other components (such as the processor 221, memory 223, and the communication device 226) of the medical device 202. Although not shown, an electrical power supply for supplying electrical power may similarly be included in each of the sensor 204, the smart accessory device 207 and the management device (PDM) 206.

The blood glucose sensor 204 may be a device communicatively coupled to the processor 261 or 221 and may be operable to measure a blood glucose value at a predetermined time interval, such as every 5 minutes, or the like. The blood glucose sensor 204 may provide a number of blood glucose measurement values to the AP applications operating on the respective devices.

The medical device 202 may provide insulin the stored in reservoir 225 to the user based on information (e.g., blood glucose measurement values) provided by the sensor 204 and/or the management device (PDM) 206. For example, the medical device 202 may contain analog and/or digital circuitry that may be implemented as a processor 221 (or controller) for controlling the delivery of the drug or therapeutic agent. The circuitry used to implement the processor 221 may include discrete, specialized logic and/or components, an application-specific integrated circuit, a microcontroller or processor that executes software instructions, firmware, programming instructions or programming code (enabling, for example, the artificial pancreas application (AP App) 229 as well as the process examples of FIGS. 1 and 3) stored in memory 223, or any combination thereof. For example, the processor 221 may execute a control algorithm, such as an artificial pancreas application 229, and other programming code that may make the processor 221 operable to cause the pump to deliver doses of the drug or therapeutic agent to a user at predetermined intervals or as needed to bring blood glucose measurement values to a target blood glucose value. In an example, the AP App 229 may include programming code that is operable upon execution by the processor 221 to provide the example processes for adjusting or modifying insulin-carbohydrate ratio and total daily insulin settings as described with reference to FIGS. 1A, 1B, 1C, 3 and 4. The size and/or timing of the doses may be programmed, for example, into an artificial pancreas application 229 by the user or by a third party (such as a health care provider, medical device manufacturer, or the like) using a wired or wireless link, such as 220, between the medical device 202 and a management device 206 or other device, such as a computing device at a healthcare provider facility. In an example, the pump or medical device 202 is communicatively coupled to the processor 261 of the management device via the wireless link 220 or via a wireless link, such as 291 from smart accessory device 207 or 208 from the sensor 204. The pump mechanism 224 of the medical device may be operable to receive an actuation signal from the processor 261, and in response to receiving the actuation signal, expel insulin from the reservoir 225 according to the set insulin bolus dosage.

The other devices in the system 200, such as management device 206, smart accessory device 207 and sensor 204, may also be operable to perform various functions including controlling the medical device 202. For example, the management device 206 may include a communication device 264, a processor 261, and a management device memory 263. The management device memory 263 may store an instance of the AP application 269 that includes programming code, that when executed by the processor 261 provides the process examples described with reference to the examples of FIGS. 1 and 3. The management device memory 263 may also store programming code for providing the process examples described with reference to the examples of FIGS. 1 and 3-7.

The smart accessory device 207 may be, for example, an Apple Watch®, other wearable smart device, including eyeglasses, provided by other manufacturers, a global positioning system-enabled wearable, a wearable fitness device, smart clothing, or the like. Similar to the management device 206, the smart accessory device 207 may also be operable to perform various functions including controlling the medical device 202. For example, the smart accessory device 207 may include a communication device 274, a processor 271, and a memory 273. The memory 273 may store an instance of the AP application 279 that includes programming code for providing the process examples described with reference to the examples of FIGS. 1 and 3-7. The memory 273 may also as store programming code and be operable to store data related to the AP application 279. The sensor 204 of system 200 may be a continuous glucose monitor (CGM) as described above, that may include a processor 241, a memory 243, a sensing or measuring device 244, and a communication device 246. The memory 243 may store an instance of an AP application 249 as well as other programming code and be operable to store data related to the AP application 249. The AP application 249 may also include programming code for providing the process examples described with reference to the examples of FIGS. 1 and 3-7.

Instructions for determining the delivery of the drug or therapeutic agent (e.g., as a bolus dosage) to the user (e.g., the size and/or timing of any doses of the drug or therapeutic agent) may originate locally by the medical device 202 or may originate remotely and be provided to the medical device 202. In an example of a local determination of drug or therapeutic agent delivery, programming instructions, such as an instance of the artificial pancreas application 229, stored in the memory 223 that is coupled to the medical device 202 may be used to make determinations by the medical device 202. In addition, the medical device 202 may be operable to communicate with the cloud-based services 211 via the communication device 226 and the communication link 288.

Alternatively, the remote instructions may be provided to the medical device 202 over a wired or wireless link by the management device (PDM) 206, which has a processor 261 that executes an instance of the artificial pancreas application 269, or the smart accessory device 207, which has a processor 271 that executes an instance of the artificial pancreas application 269 as well as other programming code for controlling various devices, such as the medical device 202, smart accessory device 207 and/or sensor 204. The medical device 202 may execute any received instructions (originating internally or from the management device 206) for the delivery of the drug or therapeutic agent to the user. In this way, the delivery of the drug or therapeutic agent to a user may be automated.

In various examples, the medical device 202 may communicate via a wireless link 220 with the management device 206. The management device 206 may be an electronic device such as, for example, a smart phone, a tablet, a dedicated diabetes therapy management device, or the like. The management device 206 may be a wearable wireless accessory device. The wireless links 208, 220, 222, 291, 292 and 293 may be any type of wireless link provided by any known wireless standard. As an example, the wireless links 208, 220, 222, 291, 292 and 293 may enable communications between the medical device 202, the management device 206 and sensor 204 based on, for example, Bluetooth®, Wi-Fi®, a near-field communication standard, a cellular standard, or any other wireless optical or radio-frequency protocol.

The sensor 204 may be a glucose sensor operable to measure blood glucose and output a blood glucose value or data that is representative of a blood glucose value. For example, the sensor 204 may be a glucose monitor or a continuous glucose monitor (CGM). The sensor 204 may include a processor 241, a memory 243, a sensing/measuring device 244, and communication device 246. The communication device 246 of sensor 204 may include one or more sensing elements, an electronic transmitter, receiver, and/or transceiver for communicating with the management device 206 over a wireless link 222 or with medical device 202 over the link 208. The sensing/measuring device 244 may include one or more sensing elements, such as a glucose measurement, heart rate monitor, or the like. The processor 241 may include discrete, specialized logic and/or components, an application-specific integrated circuit, a microcontroller or processor that executes software instructions, firmware, programming instructions stored in memory (such as memory 243), or any combination thereof. For example, the memory 243 may store an instance of an AP application 249 that is executable by the processor 241.

Although the sensor 204 is depicted as separate from the medical device 202, in various examples, the sensor 204 and medical device 202 may be incorporated into the same unit. That is, in various examples, the sensor 204 may be a part of the medical device 202 and contained within the same housing of the medical device 202 (e.g., the sensor 204 may be positioned within or embedded within the medical device 202). Glucose monitoring data (e.g., measured blood glucose values) determined by the sensor 204 may be provided to the medical device 202, smart accessory device 207 and/or the management device 206 and may be used to determine a bolus dosage of insulin for automated delivery of insulin by the medical device 202.

The sensor 204 may also be coupled to the user by, for example, adhesive or the like and may provide information or data on one or more medical conditions and/or physical attributes of the user. The information or data provided by the sensor 204 may be used to adjust drug delivery operations of the medical device 202.

In an example, the management device 206 may be a computing device operable to manage a personal diabetes treatment plan. The management device 206 may be used to program or adjust operation of the medical device 202 and/or the sensor 204. The management device 206 may be any portable electronic, computing device including, for example, a dedicated controller, such as processor 261, a smartphone, or a tablet. In an example, the management device (PDM) 206 may include a processor 261, a management device management device memory 263, and a communication device 264. The management device 206 may contain analog and/or digital circuitry that may be implemented as a processor 261 (or controller) for executing processes to manage a user's blood glucose levels and for controlling the delivery of the drug or therapeutic agent to the user. The processor 261 may also be operable to execute programming code stored in the management device management device memory 263. For example, the management device management device memory 263 may be operable to store an artificial pancreas application 269 that may be executed by the processor 261. The processor 261 may when executing the artificial pancreas application 269 may be operable to perform various functions, such as those described with respect to the examples in FIGS. 1 and 3. The communication device 264 may be a receiver, a transmitter, or a transceiver that operates according to one or more radio-frequency protocols. For example, the communication device 264 may include a cellular transceiver and a Bluetooth transceiver that enables the management device 206 to communicate with a data network via the cellular transceiver and with the sensor 204 and the medical device 202. The respective transceivers of communication device 264 may be operable to transmit signals containing information useable by or generated by the AP application or the like. The communication devices 226, 246 and 276 of respective medical device 202, sensor 204 and smart accessory device 207 may also be operable to transmit signals containing information useable by or generated by the AP application or the like.

The medical device 202 may communicate with the sensor 204 over a wireless link 208 and may communicate with the management device 206 over a wireless link 220. The sensor 204 and the management device 206 may communicate over a wireless link 222. The smart accessory device 207, when present, may communicate with the medical device 202, the sensor 204 and the management device 206 over wireless links 291, 292 and 293, respectively. The wireless links 208, 220, 222, 291, 292 and 293 may be any type of wireless link operating using known wireless standards or proprietary standards. As an example, the wireless links 208, 220, 222, 291, 292 and 293 may provide communication links based on Bluetooth®, Wi-Fi, a near-field communication standard, a cellular standard, or any other wireless protocol via the respective communication devices 226, 246 and 264. In some examples, the medical device 202 and/or the management device 206 may include a user interface 227, 278 and 268, respectively, such as a keypad, a touchscreen display, levers, buttons, a microphone, a speaker, a display, or the like, that is operable to allow a user to enter information and allow the management device to output information for presentation to the user.

In various examples, the drug delivery system 200 may be an insulin drug delivery system. In various examples, the medical device 202 may be the OmniPod® (Insulet Corporation, Billerica, Mass.) insulin delivery device as described in U.S. Pat. Nos. 7,303,549, 7,137,964, or U.S. Pat. No. 6,740,059, each of which is incorporated herein by reference in its entirety.

In various examples, the drug delivery system 200 may implement the artificial pancreas (AP) algorithm (and/or provide AP functionality) to govern or control automated delivery of insulin to a user (e.g., to maintain euglycemia—a normal level of glucose in the blood). The AP application may be implemented by the medical device 202 and/or the sensor 204. The AP application may be used to determine the times and dosages of insulin delivery. In various examples, the AP application may determine the times and dosages for delivery based on information known about the user, such as the user's sex, age, weight, or height, and/or on information gathered about a physical attribute or condition of the user (e.g., from the sensor 204). For example, the AP application may determine an appropriate delivery of insulin based on glucose level monitoring of the user through the sensor 204. The AP application may also allow the user to adjust insulin delivery. For example, the AP application may allow the user to issue (e.g., via an input) commands to the medical device 202, such as a command to deliver an insulin bolus. In some examples, different functions of the AP application may be distributed among two or more of the management device 206, the medical device (pump) 202 or the sensor 204. In other examples, the different functions of the AP application may be performed by one device, such the management device 206, the medical device (pump) 202 or the sensor 204. In various examples, the drug delivery system 200 may operate according to or may include features or functionalities of the drug delivery systems described in U.S. patent application Ser. No. 15/359,187, filed Nov. 22, 2016, which is incorporated herein by reference in its entirety.

As described herein, the drug delivery system 200 or any component thereof, such as the medical device may be considered to provide AP functionality or to implement an AP application. Accordingly, references to the AP application (e.g., functionality, operations, or capabilities thereof) are made for convenience and may refer to and/or include operations and/or functionalities of the drug delivery system 200 or any constituent component thereof (e.g., the medical device 202 and/or the management device 206). The drug delivery system 200—for example, as an insulin delivery system implementing an AP application—may be considered to be a drug delivery system or an AP application-based delivery system that uses sensor inputs (e.g., data collected by the sensor 204).

In an example, one or more of the devices, 202, 204, 206 or 207 may be operable to communicate via a wireless communication link 288 with cloud-based services 211. The cloud-based services 211 may utilize servers and data storage (not shown). The communication link 288 may be a cellular link, a Wi-Fi link, a Bluetooth link, or a combination thereof, that is established between the respective devices 202, 204, 206 or 207 of system 200. The data storage provided by the cloud-based services 211 may store anonymized data, such as user weight, blood glucose measurements, age, meal carbohydrate information, or the like. In addition, the cloud-based services 211 may process the anonymized data from multiple users to provide generalized information related to the various parameters used by the AP application. For example, an age-based general target blood glucose value may be derived from the anonymized data, which may be helpful when a user first begins using a system such as 200. The cloud-based services 211 may also provide processing services for the system 200, such as performing the process 100 in the example of FIG. 2 or additional processes, such as that described below with reference to FIG. 3.

In an example, the device 202 includes a communication device 264, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 211. For example, outputs from the sensor 204 or the medical device (pump) 202 may be transmitted to the cloud-based services 211 for storage or processing via the transceivers of communication device 264. Similarly, medical device 202, management device 206 and sensor 204 may be operable to communicate with the cloud-based services 211 via the communication link 288.

In an example, the respective receiver or transceiver of each respective device, 202, 206 or 207, may be operable to receive signals containing respective blood glucose measurement values of the number of blood glucose measurement values that may be transmitted by the sensor 204. The respective processor of each respective device 202, 206 or 207 may be operable to store each of the respective blood glucose measurement values in a respective memory, such as 223, 263 or 273. The respective blood glucose measurement values may be stored as data related to the artificial pancreas algorithm, such as 229, 249, 269 or 279. In a further example, the AP application operating on any of the management device 206, the smart accessory device 207, or sensor 204 may be operable to transmit, via a transceiver implemented by a respective communication device, 264, 274, 246, a control signal for receipt by a medical device. In the example, the control signal may indicate an amount of insulin to be expelled by the medical device 202.

Various operational scenarios and examples of processes performed by the system 200 are described herein. For example, the system 200 may be operable to implement the process examples of FIG. 1A-C. In addition, the system 200 may be operable to implement a process that accounts for periodic advanced TDI adaptivity using past glucose control performance as described with reference to FIG. 3.

FIG. 3 illustrates a process example for determining periodic advanced TDI adaptivity using past glucose control performance.

In the example of FIG. 3, a user's TDI may be adapted based on glucose control performance which enables a more accurate value of the parameter to be achieved. The determination of the TDI parameter can be calculated by either taking the entire glucose control performance into account or taking individual point-wise blood glucose measurement values provided by a continuous glucose monitor (CGM).

The difference between daily mean glucose and the user's desired control target can be related to the user's correction factor (CF) to calculate additional insulin that the user may need throughout the day. In the example, a CGM provides performs a blood glucose measurement in approximately 5 minute intervals). In the example process of FIG. 3, the artificial pancreas application may calculate a point-wise excursion between the user's blood glucose measurements versus the user's target blood glucose setting. The point-wise excursion may be incorporated to generate an overall sum of additional insulin that the user may need at each cycle.

Prior implementations may make a total daily insulin (TDI) estimation by taking the sum of an insulin pump user's daily insulin deliveries across multiple days (i.e. one week) and taking the average of the sums as the estimate. However, TDI estimates made in the manner of prior implementations may accidently omit dosages delivered manually (i.e., manual injections) or other under or over reporting of delivery of insulin. Further, an average of past insulin deliveries indicates the dosage that the user is comfortable with, but it does not necessarily indicate that the past insulin deliveries were well matched to the user's needs. For instance, if the user's average glucose concentration was very high, e.g. above the hyperglycemic threshold of 180 mg/dL, then the average insulin delivery during this period most likely does not represent the optimal insulin delivery value needed by the user.

TDI may be an input into the automatic insulin delivery algorithm utilized by the artificial pancreas application. Modification of total daily insulin (TDI) may be determined based on incorporation of daily mean blood glucose measurement values. In the example of FIG. 3, the mean of the user's blood glucose measurements may be incorporated in addition to the user's new insulin delivery values to generate a new TDI value that more accurately reflects the user's insulin needs. For example, the process 300 may include a step of retrieving a prior TDI, the prior TDI may be the current TDI used by the artificial pancreas application to make insulin dosage calculations (310). In the example of Equation No. 3 below, the current TDI may be $TDI_{old}$.

In the first factor, the retrieved TDI (i.e., $TDI_{old}$) may be multiplied by a first coefficient that indicates a confidence level of the TDI setting. This first factor may be a prior TDI contribution term. The artificial pancreas application may set the coefficient value to a higher value (e.g., closer to 1.0) to correspond with a higher level of confidence. For example, the consistency of the blood glucose measurement values may be used to determine coefficient values—more consistent blood glucose measurement values within a normal range may cause greater confidence while blood glucose measurement values within a normal range being less consistent may cause lower confidence. Based on the consistency of the blood glucose measurements, the artificial pancreas application may determine the value of the first confidence coefficient. To obtain the prior TDI contribution term, the retrieved total daily insulin may be multiplied by the first confidence coefficient (320). In the example of Equation No. 3, the prior TDI contribution term may be ($0.8*TDI_{old}$). The first confidence coefficient may be 0.8. Of course, the value of the first confidence may have different values, such as 0.2, 0.5, 0.6 or the like, as determined by the artificial pancreas application.

The process 300 may determine the average excursion of the blood glucose measurements from blood glucose target settings as represented by the second factor in the example of Equation No. 3. For example, the artificial pancreas application may obtain after a predetermined period of time, such as 12 hours, 24 hours, 48 hours, or the like, the mean of the blood glucose measurement values collected during the predetermined period of time (i.e., (G)) (330). The artificial pancreas application may further obtain the target blood glucose measurement settings for the determined period of time. Using the obtained target blood glucose measurement settings, the mean target blood glucose measurement setting (i.e., (target)) may be determined for the predetermined period of time. This may be considered be a correction factor that is determined as a point-wise excursion between the user's glucose versus the user's target, calculated during each 5 minute interval. For example, a difference between the mean of the blood glucose measurement values and the blood glucose target settings may be determined by the artificial pancreas application. The determined difference is the numerator of the second factor. The artificial pancreas application may proceed to determining the denominator of the second factor. The denominator may be a correction factor that may be determined utilizing different rules of thumb based on the type of insulin being used and a TDI setting. For example, if the user is using fast acting insulin, a value of 1800 may be divided by the retrieved total daily insulin setting (i.e., $TDI_{old}$) to calculate the correction factor value. Alternatively, if the user is using regular action insulin, a value of 1500 may be divided by the retrieved total daily insulin setting (i.e., $TDI_{old}$) to calculate the correction factor value.

The second term in Equation 3 below may be a correction factor determined by dividing the difference in the numerator by the correction factor (e.g., the 1800 rule) of the denominator to calculate the missing or excess insulin delivery throughout the day. The correction factor can be incorporated in the equation (Eq. 3) to generate an overall sum of additional insulin that the user may need at each cycle. A cycle being the time period that the new TDI is calculated. For example, a cycle may be 24 hours, 12 hours 8 hours or the like.

In one example, this adjustment can be implemented as shown in Equation No. 3 below:

$$TDI_{new3} = 0.8TDI_{old} + 8\frac{\overline{G} - \overline{target}}{1800/TDI_{old}} + 0.2\sum_{t=1}^{288} I(t) \qquad \text{Eq. No. 3}$$

where ($\overline{G}$) may be the mean of the blood glucose measurement values collected during the predetermined period of time, $\overline{target}$ may be the mean of the blood glucose measurement target values during the predetermined period of time and I(t) is the insulin delivered at time t.

In the second term of equation No. 3 example, the coefficient of 8 represents 24 hours divided by different segments of 3 hours each, given the assumption that it will take a number of hours approximately equal to the duration of insulin action (DIA) for a user to reduce the mean blood glucose measurement to the target blood glucose setting. The correction factor (for example, $1800ITDI_{old}$) in the denominator of the second factor incorporates the 1800 rule instead of utilizing the user's correction factor (CF) to reduce vulnerability to human error. Of course, other rules, such as the 1500 rule, may be used.

The third term may be a delivered TDI factor that is determined using data collected by the artificial pancreas application at 340. Since the artificial pancreas application controls how much insulin is delivered, the artificial pancreas application may store the amount of insulin delivered with each dose in a memory coupled to the processor executing the artificial pancreas application. For example, the artificial pancreas application may deliver insulin is a number of small doses over a period of time. In the example of Equation No. 3, the summation of the delivered insulin is over 288 doses of insulin. In this example, the insulin may be delivered every 5 minutes or 12 time an hour. Over a period of 24 hours, the artificial pancreas application sends instructions for the delivery of 288 doses of insulin. In addition, this sum of delivered insulin may be multiplied by a second confidence factor that is the difference between 1.0 and the first confidence factor. In the example of Equation No. 3, the first confidence factor to 0.8, so the difference between 1.0 and 0.8 is 0.2.

At 350, a new TDI setting (i.e., $TDI_{new3}$) may be determined by summing the prior TDI contribution term, the correction factor term and the delivered insulin term. Based on the new TDI setting, the artificial pancreas application may modify a next delivery of insulin (360). For example, a new insulin dosage may be determined, and the delivery of insulin may be actuated by the artificial pancreas application.

Of course, different numbers used in Equation No. 3 may be parameterized. For example, the first and second confidence factors may be parameterized so that some of the changes to the user's blood glucose measurements may occur more quickly. For example, the first confidence factor may be set to 0.5 in which case the second confidence factor may also be 0.5. In addition, the coefficient 8 in the second factor may be based on the duration of insulin action (DIA). If the user's DIA is 6 hours instead of the 3 hours in the example of Equation No. 3, then the coefficient may be 4 (i.e., 24 hours/6=4).

In another example, the adjustment to TDI may be segmented to avoid adjusting the TDI if the mean glucose blood glucose measurement is close to the target and to reduce vulnerability to noise, as shown in Equation No. 4 shown below:

$$TDI_{new4} = 0.8TDI_{old} + 8I_e + 0.2\sum_{t=1}^{288} I(t);$$

$$I_e = \begin{cases} \text{abs}(\overline{G} - \overline{target}) > 40 & \frac{\overline{G} - \overline{target}}{1800/TDI_{old}} \\ \text{abs}(\overline{G} - \overline{target}) \le 40 & 0 \end{cases}$$

In the example of Equation No. 4, the threshold of 40 (mg/dL) that is compared to the excursion of the blood glucose measurements from the target blood glucose measurement setting is selected based on the correction factor. The correction factor may be close to 40 for a typical user, the basis for the selection of 40 is that at times the excursions in blood glucose measurements may be due to noise or other extraneous inputs and the threshold 40 represents a reciprocal of the correction factor and is approximately equivalent to one unit of insulin. This is intended to avoid over compensating for excursions in the blood glucose measurements.

In another example, the TDI modification that produces $TDI_{new4}$ may be based on a point-by-point residual insulin needs after an IOB is determined.

For example, point-by-point excursions of the user's blood glucose measurements versus the user's blood glucose measurement target setting may be related to the user's correction factor to enable the artificial pancreas application to adjust the user's TDI dynamically.

In another example, the modification of TDI based on point-by-point residual insulin needs after an insulin onboard (IOB) is provided may be determined as shown in the example of equation no. 5 and FIG. 4. This may be a periodic adjustment or modification of TDI.

In an example shown in Equation No. 5, this adjustment can be implemented as:

$$TDI_{new5} = 0.8TDI_{old} + 0.2\sum_{t=1}^{288} I(t) + \frac{\frac{G(t) - \text{target}(t)}{1800/TDI} - IOB(t)}{36} \qquad \text{Eq. No. 5}$$

In the process 400 of FIG. 4, the artificial pancreas application executed by the processor may, at 410, obtain a current TDI setting (e.g., $TDI_{old}$) either from a memory or user input. At 420, the artificial pancreas application may determine a first factor in a new TDI function of Equation No. 5 using the current TDI setting by multiplying the current TDI by a first coefficient, where the first coefficient indicates a confidence level of the TDI setting. This first factor may be a prior TDI contribution term. The artificial pancreas application may set the coefficient value a higher to correspond with a higher level of confidence. At 430, the artificial pancreas application may determine a second factor in the new TDI function (Equation No. 5) by retrieving amounts of insulin delivered over a period of time, such as every 5 minutes over 24 hours or 288 delivered doses, summing the amounts of insulin delivered, and multiplying the sum by a second confidence factor. Note similar to the earlier examples the first and second confidence factors in this example when added together equal 1.0 (e.g., 0.8+ 0.2=1.0). In other examples, the first and second confidence values may equal a value different from 1.0.

In process 400, a third factor may be determined, at 440, that accounts for the excursions of IOB that occur in 3 hour increments and since there are 12 blood glucose measurements received every hour (e.g., 3 time 12 equals 36). The third factor accounts for the deviation of blood glucose measurements from target blood glucose measurement settings (e.g., G(t))–target (t)) which is converted to an amount of insulin by dividing that difference using the 1800 rule (which may be a 1500 rule or the like depending upon the type of insulin being used (e.g., fast acting versus regular acting).

Upon the determination of the third factor, the artificial pancreas application may sum the first factor, the second factor and the third factor to arrive at a new TDI (i.e., $TDI_{new5}$) at 450. The new TDI (i.e., $TDI_{new2}$) may be used by the artificial pancreas application in the calculation of a new dosage of insulin to be provided by a drug delivery device to the user. Upon calculating the new dosage of insulin, the artificial pancreas application may generate control commands that are sent to the drug delivery device instructing the drug delivery device to deliver a dose of insulin according the control command (460). The dose of insulin may be delivered by the drug delivery device according to the control command.

The foregoing process may also be implemented using other equations, such as equation nos. 6 and 7 below, related to the determination of TDI based on the insulin onboard.

In another example, this adjustment can be conducted in real time, as:

$$TDI(t+1) = \frac{287 \cdot TDI(t)}{288} + I(t) + \frac{\frac{G(t) - \text{target}(t)}{1800/TDI} - IOB(t)}{36} \quad \text{Eq. No. 6}$$

where the factors 287/288 represent the number of five-minute control cycles in one day minus 1 and the number of five-minute control cycles in one day, respectively. Calculation of TDI in this manner allows a revised "moving average" of the TDI that is recalculated at every 5 minute cycle.

In other examples, the periodicity of TDI adjustments for either option does not need to be either real-time or daily—the factors of 0.8 and 0.2 can be made variable depending on the duration of available data, as:

$$TDI_{new7} = (1 - 0.2 \cdot T_{new})TDI_{old} + \quad \text{Eq. No. 7}$$

$$8\frac{T_{new}}{288} + \frac{\overline{G} - \overline{\text{target}}}{1800/TDI_{old}} + 0.2 \cdot T_{new} \sum_{t=1}^{T_{new}} I(t)$$

where $T_{new}$ is a number of new 5 minute segments of data available at time of TDI adjustment.

In the example of Eq. 7, the factor 8 represents the maximum duration of insulin action, to apply a conservative estimate of TDI modification assuming that an increase in glucose can be covered by 8 hours of insulin delivery. This value can be adjusted as a tuning parameter to different values, such as 2, 3, 4, 5, 6, 7, or 8. Thus, the first term represents the duration of time of new data available ("weighing of the previous TDI estimate"), the second term represents adjustment of the current TDI estimate based on deviation in average glucose during this new data versus the target, modified by duration in insulin action, and the third term represents the actual insulin delivery that occurred during this period of new data.

The techniques described herein for providing a determination of a new insulin-to-carbohydrate ratio and a new total daily insulin factor for a drug delivery system (e.g., the system 200 or any component thereof) may be implemented in hardware, software, or any combination thereof. For example, the system 200 or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some embodiments, the techniques described herein, and/or any system or constituent component described herein may be implemented with a processor executing computer readable instructions stored on one or more memory components.

Some embodiments of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with embodiments of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A device, comprising:
   a processor; and
   a memory storing programming code, an artificial pancreas application, and operable to store data related to the artificial pancreas application, wherein the programming code and the artificial pancreas application are executable by the processor,
   wherein the processor when executing the artificial pancreas application is operable to control delivery of insulin, and to perform functions, including functions to:
   receive an approximate amount of carbohydrates ingested in a meal;
   determine an amount of insulin onboard in a post prandial time period;
   determine an error factor representing an amount of insulin over or under delivered during the post prandial period;
   determine a difference between the determined amount of insulin onboard and the error factor;
   calculate an updated insulin to carbohydrate ratio based on the determined difference and the approximate amount of carbohydrates ingested; and
   modify delivery of insulin based on the updated insulin to carbohydrate ratio.

2. The device of claim 1, further comprises:
   a blood glucose sensor communicatively coupled to the processor and operable to measure a blood glucose value at a predetermined time interval; and
   provides the measured blood glucose value to the processor and the artificial pancreas application.

3. The device of claim 1, wherein the processor when executing the artificial pancreas application is further operable to:
   retrieve a total daily insulin (TDI) setting;
   multiply the retrieved TDI setting by a first confidence coefficient to provide a prior total daily insulin contribution term;
   determine an average excursion of blood glucose measurement from target;
   determine a delivered TDI factor based on the amount of insulin delivered since the TDI setting was set;
   determine a new TDI setting by summing a prior total daily insulin contribution term, a correction factor, and a delivered insulin term; and
   modify a next delivery of insulin based on the new TDI.

4. The device of claim 3, wherein the processor is further operable to:
   multiply the retrieved TDI by a first coefficient to provide a prior TDI contribution term, wherein the first coefficient indicates a confidence level of the TDI setting, and the higher the coefficient value the higher the level of confidence.

5. The device of claim 1, further comprises:
   a blood glucose sensor communicatively coupled to the processor, wherein the blood glucose sensor is operable to:
   measure a blood glucose value at a predetermined time interval; and
   provide the measured blood glucose value to the processor and the artificial pancreas application.

6. The device of claim 1, wherein the processor when executing the artificial pancreas application is further operable to:
   determine that a meal has been ingested or to be ingested;
   monitor delivery of insulin over a period of time in response to the determination that a meal has been ingested or to be ingested; and
   use an amount of insulin delivered over the period of time in the determination of the amount of insulin onboard in the post prandial time period.

7. The device of claim 1, wherein the processor when determining the error factor is further operable to:
   determine a difference between a received blood glucose measurement to a target blood glucose setting for each of a plurality of received blood glucose measurements;
   sum the differences during the post prandial period; and
   obtain the error factor by dividing the summed differences by a correction factor that accounts for a user's ability to process delivered insulin.

8. The device of claim 1, wherein the modified delivery of insulin may be a newly calculated amount of insulin to be delivered in a next dosage, or as a modification of the amount of insulin to be delivered and a time of the delivery of a next dose of insulin.

9. The device of claim 1, wherein the processor is further operable to:
actuate the pump mechanism to deliver a next insulin dose based on a calculated insulin dosage using the updated insulin to carbohydrate ratio.

10. The device of claim 1, further comprising:
a transceiver operable to receive and transmit signals containing information usable by or generated by the artificial pancreas application.

11. The device of claim 1, wherein the difference between the determined amount of insulin onboard and the error factor provides an estimated amount of insulin to compensate for ingestion of the meal.

12. A non-transient computer readable medium embodied with programming instructions, where the programming instructions when executed by a processor configure the processor to:
receive an approximate amount of carbohydrates ingested in a meal;
determine an amount of insulin onboard in a post prandial time period;
determine an error factor representing an amount of insulin over or under delivered during the post prandial period;
determine a difference between the determined amount of insulin onboard and the error factor;
calculate an updated insulin to carbohydrate ratio based on the determined difference and the approximate amount of carbohydrates ingested; and
modify delivery of insulin based on the updated insulin to carbohydrate ratio.

13. The computer readable medium of claim 12, further configuring the processor to:
receive, from a blood glucose sensor communicatively coupled to the processor, a blood glucose value at a predetermined time interval.

14. The computer readable medium of claim 12, further configuring the processor to:
retrieve a total daily insulin (TDI) setting;
multiply the retrieved TDI setting by a first confidence coefficient to provide a prior total daily insulin contribution term;
determine an average excursion of blood glucose measurement from target;
determine a delivered TDI factor based on the amount of insulin delivered since the TDI setting was set;
determine a new TDI setting by summing a prior total daily insulin contribution term, a correction factor, and a delivered insulin term; and
modify a next delivery of insulin based on the new TDI.

15. The computer readable medium of claim 14, further configuring the processor to:
multiply the retrieved TDI by a first coefficient to provide a prior TDI contribution term, wherein the first coefficient indicates a confidence level of the TDI setting, and the higher the coefficient value the higher the level of confidence.

16. The computer readable medium of claim 14, further configuring the processor, when modifying delivery of insulin, to:
calculate a new amount of insulin to be delivered in the next delivery of insulin, or adjust an amount of insulin to be delivered and a time of the delivery of the next delivery of insulin.

17. The computer readable medium of claim 14, further configuring the processor to:
actuate the pump mechanism to deliver a next insulin dose based on a calculated insulin dosage using the updated insulin to carbohydrate ratio.

18. The computer readable medium of claim 12, further configuring the processor to:
determine that a meal has been ingested or to be ingested;
monitor delivery of insulin over a period of time in response to the determination that a meal has been ingested or to be ingested; and
use an amount of insulin delivered over the period of time in the determination of the amount of insulin onboard in a post prandial time period.

19. The computer readable medium of claim 12, further configuring the processor, when determining the error factor, to:
determine a difference between a received blood glucose measurement and a target blood glucose setting for each of a plurality of received blood glucose measurements;
sum the differences during the post prandial period; and
obtain the error factor by dividing the summed differences by a correction factor that accounts for a user's ability to process delivered insulin.

20. The computer readable medium of claim 12, wherein the difference between the determined amount of insulin onboard and the error factor provides an estimated amount of insulin to compensate for ingestion of the meal.

* * * * *